United States Patent
Watanabe et al.

(10) Patent No.: US 10,217,630 B2
(45) Date of Patent: Feb. 26, 2019

(54) METHOD OF FORMING SILICON-CONTAINING FILM

(71) Applicant: TOKYO ELECTRON LIMITED, Tokyo (JP)

(72) Inventors: Tsubasa Watanabe, Oshu (JP); Yamato Tonegawa, Nirasaki (JP)

(73) Assignee: TOKYO ELECTRON LIMITED, Tokyo (JP)

( * ) Notice: Subject to any disclaimer, the term of this patent is extended or adjusted under 35 U.S.C. 154(b) by 0 days.

(21) Appl. No.: 15/820,489

(22) Filed: Nov. 22, 2017

(65) Prior Publication Data

US 2018/0144931 A1  May 24, 2018

(30) Foreign Application Priority Data

Nov. 24, 2016  (JP) .................................. 2016-227761
Jun. 9, 2017  (JP) .................................. 2017-114590

(51) Int. Cl.
| | |
|---|---|
| *H01L 21/02* | (2006.01) |
| *C23C 16/458* | (2006.01) |
| *C23C 16/455* | (2006.01) |
| *C23C 16/34* | (2006.01) |
| *C23C 16/44* | (2006.01) |
| *C07F 7/00* | (2006.01) |
| *H01L 27/11582* | (2017.01) |

(52) U.S. Cl.
CPC ......... *H01L 21/02211* (2013.01); *C07F 7/00* (2013.01); *C23C 16/345* (2013.01); *C23C 16/4408* (2013.01); *C23C 16/4584* (2013.01); *C23C 16/45553* (2013.01); *H01L 21/0217* (2013.01); *H01L 21/0228* (2013.01); *H01L 27/11582* (2013.01)

(58) Field of Classification Search
CPC combination set(s) only.
See application file for complete search history.

(56) References Cited

U.S. PATENT DOCUMENTS

| | | | | |
|---|---|---|---|---|
| 2016/0300715 A1* | 10/2016 | Dube | ............... | H01L 21/02532 |
| 2018/0190489 A1* | 7/2018 | Li | ................ | H01L 21/02639 |
| 2018/0204742 A1* | 7/2018 | Tateno | ............. | H01L 21/31 |
| 2018/0209063 A1* | 7/2018 | Myronov | ........... | C30B 25/02 |

FOREIGN PATENT DOCUMENTS

| | | | |
|---|---|---|---|
| JP | 05059331 A | * | 3/1993 |
| JP | 2007-299776 A | | 11/2007 |

* cited by examiner

*Primary Examiner* — Mamadou Diallo
(74) *Attorney, Agent, or Firm* — Nath, Goldberg & Meyer; Jerald L. Meyer

(57) ABSTRACT

A method of forming a silicon-containing film includes: an adsorption step of supplying a silicon-containing gas represented by a general formula $XSiCl_3$ (wherein X is an element whose bonding energy with Si is smaller than bonding energy of a Si—Cl bond) into a processing chamber accommodating substrates to cause the silicon-containing gas to be adsorbed to a surface of each of the substrates; and a reaction step of supplying a reaction gas reacting with the silicon-containing gas into the processing chamber to cause the silicon-containing gas adsorbed to the surface of each of the substrates to react with the reaction gas.

11 Claims, 18 Drawing Sheets

FIG. 17A
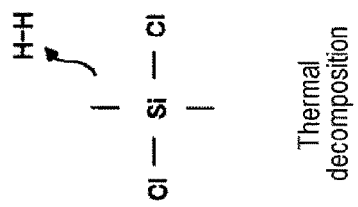
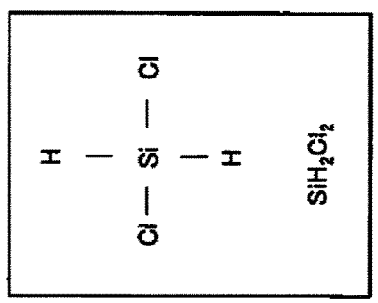
FIG. 17B
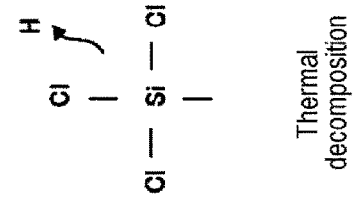
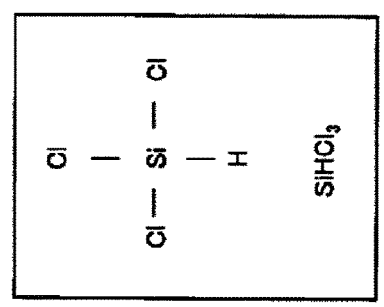

METHOD OF FORMING SILICON-CONTAINING FILM

CROSS-REFERENCE TO RELATED APPLICATIONS

This application is based upon and claims the benefit of priority from Japanese Patent Application Nos. 2016-227761 and 2017-114590, filed on Nov. 24, 2016 and Jun. 9, 2017, the entire contents of which are incorporated herein by reference.

TECHNICAL FIELD

The present disclosure relates to a method of forming a silicon-containing film.

BACKGROUND

In the related art, there is known a method of forming a silicon nitride film on a semiconductor wafer by using an ALD (Atomic Layer Deposition) method in which an adsorption step and a nitriding step are repeated.

In the case of forming a silicon nitride film on a semiconductor wafer by using an ALD method, the film formation time is shortened and the productivity is improved, for example, by a method of increasing a process temperature to enhance the adsorption efficiency of a raw material gas or a method of shortening the time of one cycle.

However, in the method of increasing the process temperature, uniformity may deteriorate due to a CVD reaction. In the method of shortening the time of one cycle, the reaction time per cycle is shortened. Therefore, the adsorption reaction and the nitriding reaction may become insufficient and the film quality may deteriorate. Thus, in the method of related art, it was difficult to achieve both the enhancement in productivity and the improvement in film quality.

SUMMARY

Some embodiments of the present disclosure provide a method of forming a silicon-containing film, which is capable of achieving both the enhancement in productivity and the improvement in film quality.

According to one embodiment of the present disclosure, there is provided a method of forming a silicon-containing film including: an adsorption step of supplying a silicon-containing gas represented by a general formula $XSiCl_3$ (wherein X is an element whose bonding energy with Si is smaller than bonding energy of a Si—Cl bond) into a processing chamber accommodating substrates to cause the silicon-containing gas to be adsorbed to a surface of each of the substrates; and a reaction step of supplying a reaction gas reacting with the silicon-containing gas into the processing chamber to cause the silicon-containing gas adsorbed to the surface of each of the substrates to react with the reaction gas.

BRIEF DESCRIPTION OF DRAWINGS

The accompanying drawings, which are incorporated in and constitute a part of the specification, illustrate embodiments of the present disclosure, and together with the general description given above and the detailed description of the embodiments given below, serve to explain the principles of the present disclosure.

FIGS. 17A and 17B are views for explaining an adsorption mechanism of a silicon-containing gas.

DETAILED DESCRIPTION

Figure 1:
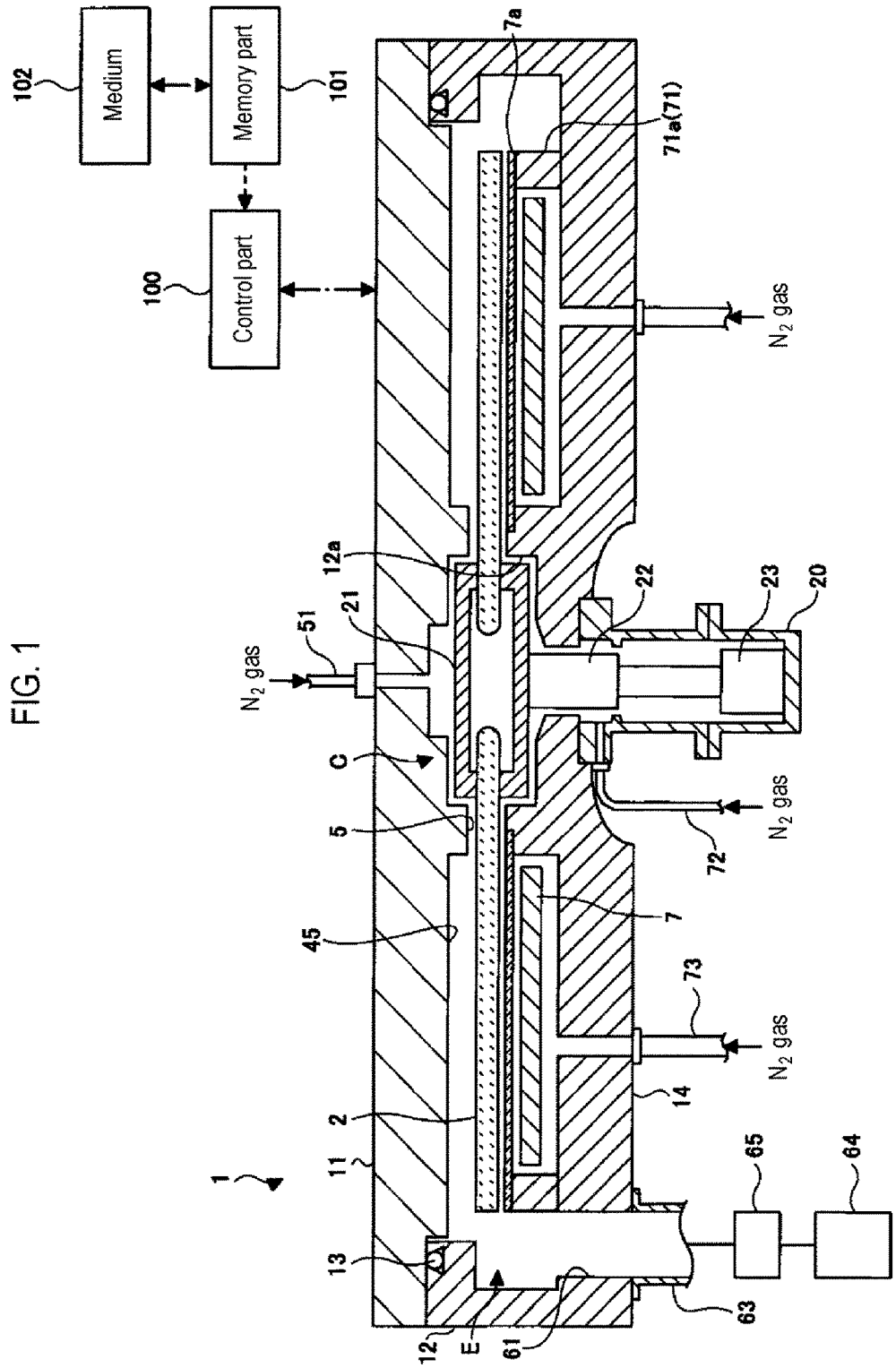
FIG. 1 is a schematic sectional view of a film forming apparatus suitable for carrying out a method of forming a silicon nitride film according to an embodiment of the present disclosure.

Hereinafter, a mode for carrying out the present disclosure will be described with reference to the drawings. In the specification and the drawings, substantially the same components are denoted by the same reference numerals, and redundant description is omitted. Reference will now be made in detail to various embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, systems, and components have not been described in detail so as not to unnecessarily obscure aspects of the various embodiments.

[First Embodiment]

In the first embodiment, as an example of a method of forming a silicon-containing film of the present disclosure, a case of forming a silicon nitride film using a semi-batch type film forming apparatus that performs a film forming process collectively on a plurality of wafers mounted on a rotary table will be described.

(Film Forming Apparatus)

Figure 2:
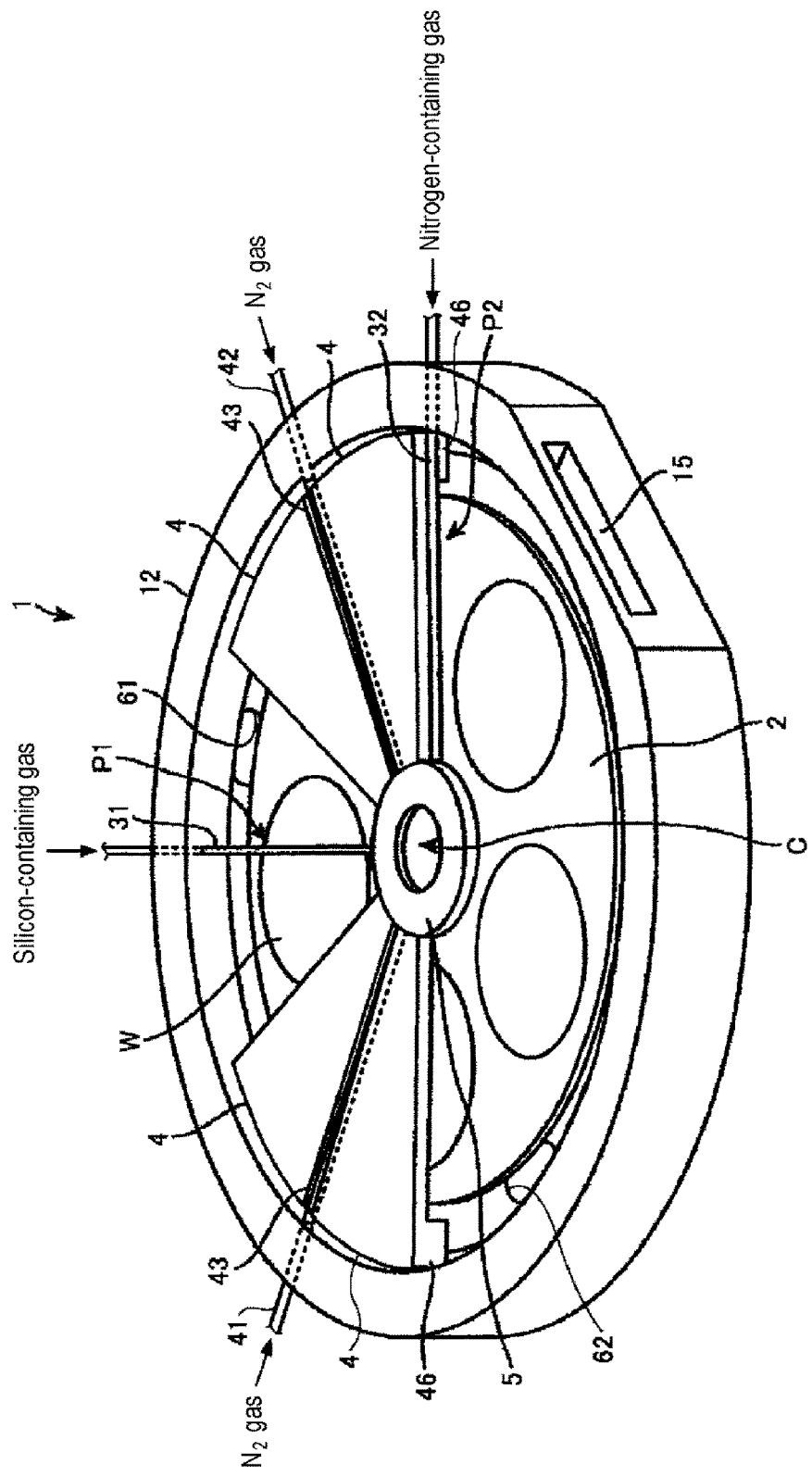
FIG. 2 is a schematic perspective view of the film forming apparatus shown in FIG. 1.
Figure 3:
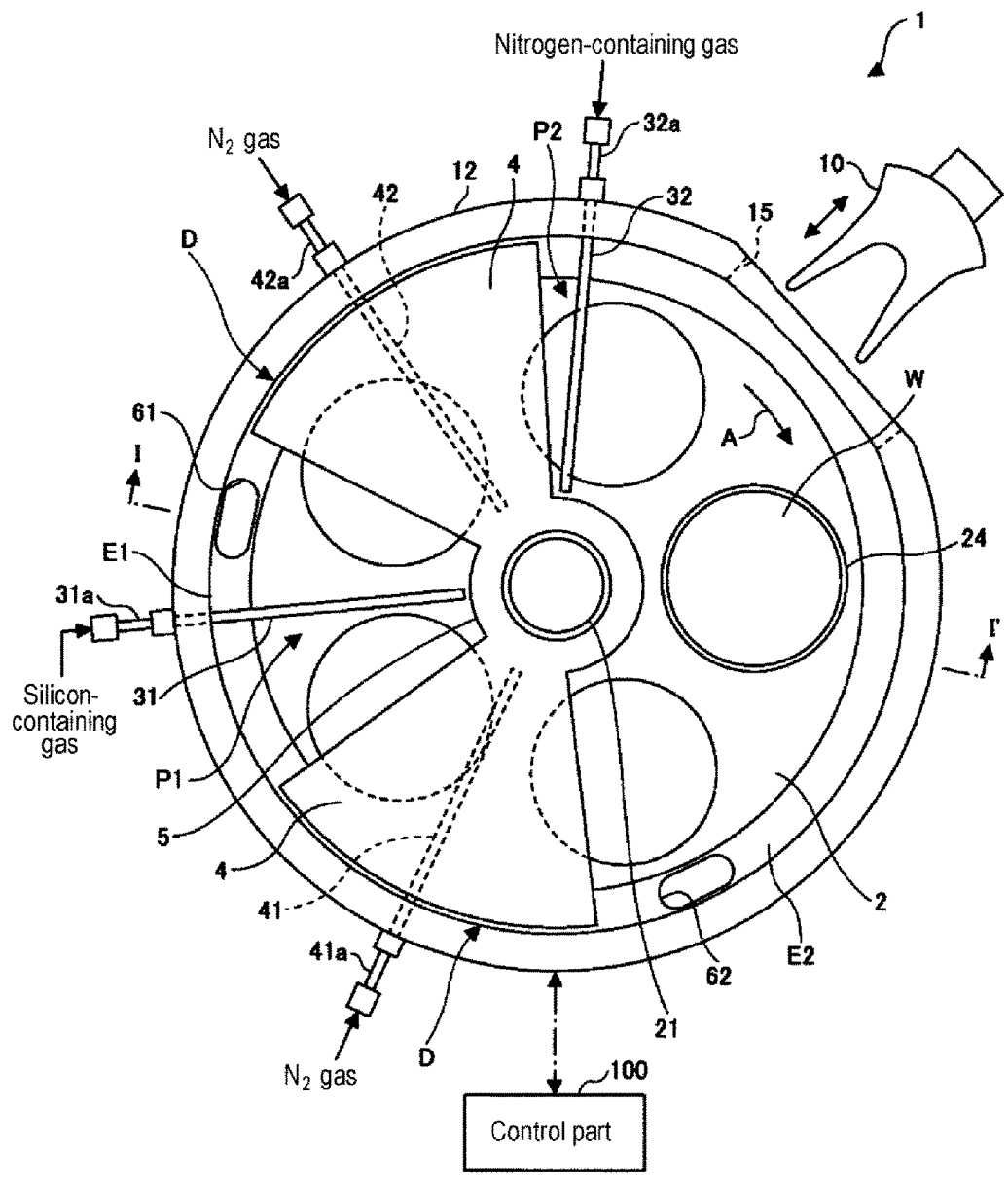
FIG. 3 is a schematic plan view showing a configuration inside a vacuum container of the film forming apparatus shown in FIG. 1.

First, a film forming apparatus suitable for carrying out a method of forming a silicon nitride film according to an embodiment of the present disclosure will be described. FIG. 1 is a schematic sectional view of a film forming apparatus suitable for carrying out a method of forming a silicon nitride film according to an embodiment of the present disclosure. FIG. 2 is a schematic perspective view of the film forming apparatus shown in FIG. 1. FIG. 3 is a schematic plan view showing a configuration inside a vacuum container of the film forming apparatus shown in FIG. 1.

Referring to FIGS. 1 to 3, the film forming apparatus includes a flat vacuum container 1 having a substantially circular plan-view shape, and a rotary table 2 provided inside the vacuum container 1 and having a rotation center at the center of the vacuum container 1. The vacuum container 1 includes a container body 12 having a bottomed cylindrical shape, and a top plate 11 airtightly and removably arranged on the upper surface of the container body 12 via a seal member 13 (FIG. 1) such as, for example, an 0 ring or the like.

The rotary table 2 is fixed to a cylindrical core portion 21 at the center portion thereof. The core portion 21 is fixed to the upper end of a rotating shaft 22 extending in the vertical direction. The rotating shaft 22 passes through a bottom portion 14 of the vacuum container 1. The lower end of the rotating shaft 22 is attached to a driving part 23 that rotates the rotating shaft 22 (FIG. 1) about a vertical axis. The rotating shaft 22 and the driving part 23 are accommodated in a tubular case body 20 whose top surface is opened. A flange portion provided on the upper surface of the case body 20 is airtightly attached to the lower surface of the bottom portion 14 of the vacuum container 1, whereby the airtight state between the internal atmosphere of the case body 20 and the external atmosphere is maintained.

On the surface portion of the rotary table 2, as shown in FIGS. 2 and 3, circular recesses 24 capable of mounting a plurality of (five, in the illustrated example) semiconductor wafers (hereinafter referred to as "wafer W") as substrates are provided along the rotation direction (circumferential direction). In FIG. 3, for the sake of convenience, the wafer W is shown to be mounted only in one recess 24. The recess 24 has an inner diameter slightly, for example, 4 mm larger than the diameter of the wafer W and a depth substantially equal to the thickness of the wafer W. Therefore, when the wafer W is accommodated in the recess 24, the surface of the wafer W and the surface of the rotary table 2 (the area where the wafer W is not mounted) have the same height. Through holes (not shown) through which, for example, three lift pins for supporting the back surface of the wafer W and moving the wafer W up and down are penetrated are formed on the bottom surface of the recess 24.

FIGS. 2 and 3 are views for explaining the structure inside the vacuum container 1. The illustration of the top plate 11 is omitted for the convenience of explanation. As shown in FIGS. 2 and 3, above the rotary table 2, reaction gas nozzles 31 and 32 and separation gas nozzles 41 and 42 made of, for example, quartz are arranged so as to be spaced apart from one another in the circumferential direction of the vacuum container 1 (the rotation direction of the rotary table 2 indicated by an arrow A in FIG. 3). In the illustrated example, the separation gas nozzle 41, the reaction gas nozzle 31, the separation gas nozzle 42, and the reaction gas nozzle 32 are arranged in the named order in the clockwise direction (the rotation direction of the rotary table 2) from a transfer port 15 described later. These nozzles 31, 32, 41, and 42 are introduced into the vacuum container 1 from the outer peripheral wall of the vacuum container 1 by fixing the gas introduction ports 31a, 32a, 41a, and 42a (FIG. 3), which are the base end portions of the nozzles 31, 32, 41, and 42, to the outer peripheral wall of the container body 12. The nozzles 31, 32, 41, and 42 are attached so as to extend horizontally with respect to the rotary table 2 along the radial direction of the container body 12.

The reaction gas nozzle 31 is connected to a silicon-containing gas supply source (not shown) via a pipe (not shown), a flow rate controller (not shown) and the like. The reaction gas nozzle 32 is connected to a nitrogen-containing gas supply source (not shown) via a pipe (not shown), a flow rate controller (not shown) and the like. Both of the separation gas nozzles 41 and 42 are connected to a separation gas supply source (not shown) via a pipe (not shown), a flow rate control valve (not shown) and the like. As a separation gas, a rare gas such as a helium (He) gas, an argon (Ar) gas or the like, or an inert gas such as a nitrogen ($N_2$) gas or the like may be used. In the present embodiment, the $N_2$ gas is used.

In the reaction gas nozzles 31 and 32, a plurality of gas discharge holes 35 opened toward the rotary table 2 are arranged at intervals of, for example, 10 mm, along the length direction of the reaction gas nozzles 31 and 32. The region under the reaction gas nozzle 31 is a first processing region P1 for causing a silicon-containing gas to be adsorbed to the wafer W. The region under the reaction gas nozzle 32 is a second processing region P2 for nitriding the silicon-containing gas adsorbed to the wafer W in the first processing region P1.

Referring to FIGS. 2 and 3, in the vacuum container 1, two convex portions 4 are provided. In order to define separation regions D together with the separation gas nozzles 41 and 42, the convex portions 4 are attached to the back surface of the top plate 11 so as to protrude toward the rotary table 2 as described later. Furthermore, the convex portion 4 has a fan-like plan-view shape with the vertex portion thereof cut in a circular arc shape. In the present embodiment, the inner circular arc of the convex portion 4 is connected to a protrusion portion 5 (described later), and the outer circular arc of the convex portion 4 is disposed so as to extend along the inner peripheral surface of the container body 12 of the vacuum container 1.

Figure 4:
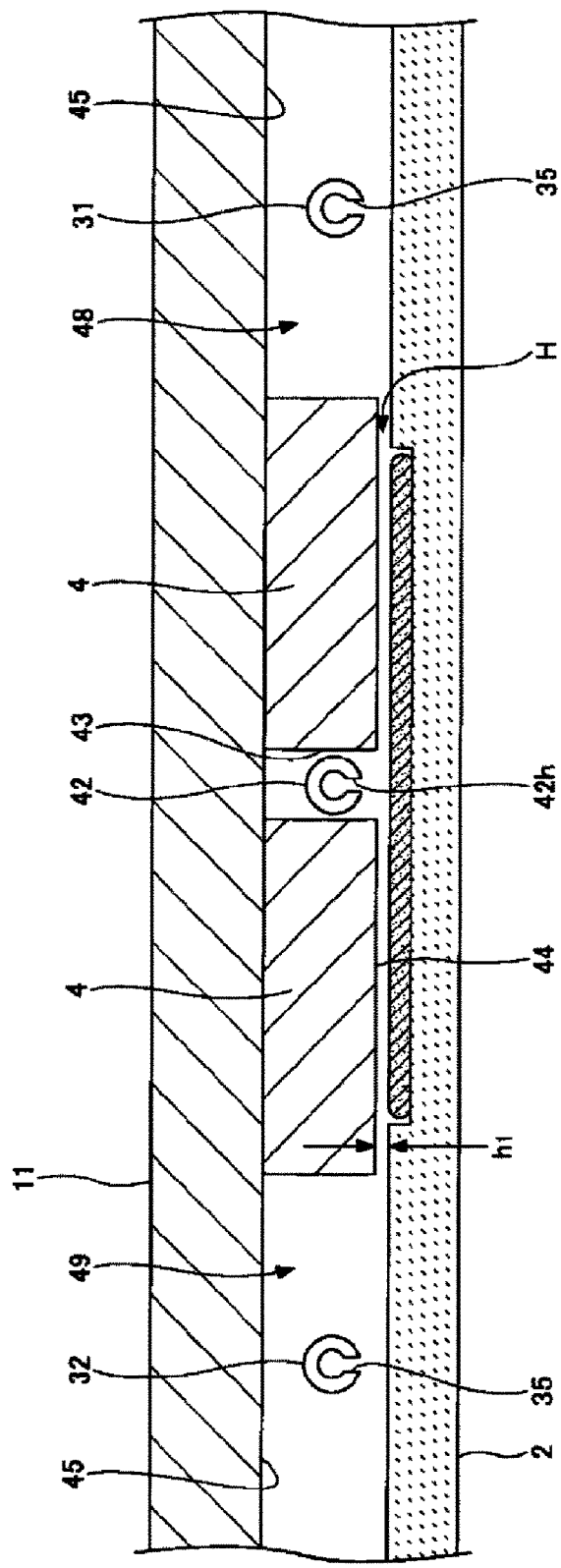
FIG. 4 is a schematic sectional view of the vacuum container taken along a concentric circle of a rotary table of the film forming apparatus shown FIG. 1.

FIG. 4 shows a cross section of the vacuum container 1 taken along the concentric circle of the rotary table 2 from the reaction gas nozzle 31 to the reaction gas nozzle 32. As shown in FIG. 4, the convex portion 4 is attached to the back surface of the top plate 11. Therefore, a flat low ceiling surface 44 (first ceiling surface), which is the lower surface of the convex portion 4, and a ceiling surface 45 (a second ceiling surface), which is located on both sides of the ceiling surface 44 in the circumferential direction and which is higher than the ceiling surface 44, are present inside the vacuum container 1. The ceiling surface 44 has a fan-like plan-view shape with the vertex thereof cut in a circular arc shape. As shown in FIG. 4, a groove portion 43 formed so as to extend in the radial direction is formed in the convex portion 4 at the circumferential center thereof. The separation gas nozzle 42 is accommodated in the groove portion 43. Similarly, a groove portion 43 is formed in another convex portion 4. The separation gas nozzle 41 is accommodated in the groove portion 43. In addition, the reaction gas nozzles 31 and 32 are respectively provided in the spaces under the high ceiling surface 45. These reaction gas nozzles 31 and 32 are spaced apart from the ceiling surface 45 and are provided in the vicinity of the wafer W. As shown in FIG. 4, the reaction gas nozzle 31 is provided in the right space 48 under the high ceiling surface 45, and the reaction gas nozzle 32 is provided in the left space 49 under the high ceiling surface 45.

In the separation gas nozzles 41 and 42 accommodated in the groove portions 43 of the convex portions 4, a plurality of gas discharge holes 41h (see FIG. 4) opened toward the rotary table 2 are arranged along the length direction of the separation gas nozzles 41 and 42 at intervals of, for example, 10 mm.

The ceiling surface 44 defines a separation space H, which is a narrow space, with respect to the rotary table 2. When an $N_2$ gas is supplied from the discharge holes 42h of the separation gas nozzle 42, the $N_2$ gas flows toward the space 48 and the space 49 through the separation space H. At this time, the pressure of the separation space H may be made higher than the pressures of the spaces 48 and 49 by the $N_2$ gas because the volume of the separation space H is smaller than the volumes of the spaces 48 and 49. That is to say, a high-pressure separation space H is formed between the spaces 48 and 49. The $N_2$ gas flowing out from the separation space H into the spaces 48 and 49 acts as a counter-flow against the silicon-containing gas from the first processing region P1 and the nitrogen-containing gas from the second processing region P2. Therefore, the silicon-containing gas from the first processing region P1 and the nitrogen-containing gas from the second processing region P2 are separated by the separation space H. Accordingly, the silicon-containing gas and the nitrogen-containing gas are prevented from mixing and reacting in the vacuum container 1.

In consideration of the pressure in the vacuum container 1, the rotation speed of the rotary table 2, the supply amount of the separation gas ($N_2$ gas) to be supplied, and the like during film formation, the height h1 of the ceiling surface 44 with respect to the upper surface of the rotary table 2 may be set to a height suitable for making the pressure in the separation space H higher than the pressures in the spaces 48 and 49.

The protrusion portion 5 (FIGS. 2 and 3) surrounding the outer periphery of the core portion 21 for fixing the rotary table 2 is provided on the lower surface of the top plate 11. In the present embodiment, the protrusion portion 5 is continuous with the portions on the rotation center side of the convex portions 4. The lower surface of the protrusion portion 5 is formed at the same height as the ceiling surface 44.

Figure 5:
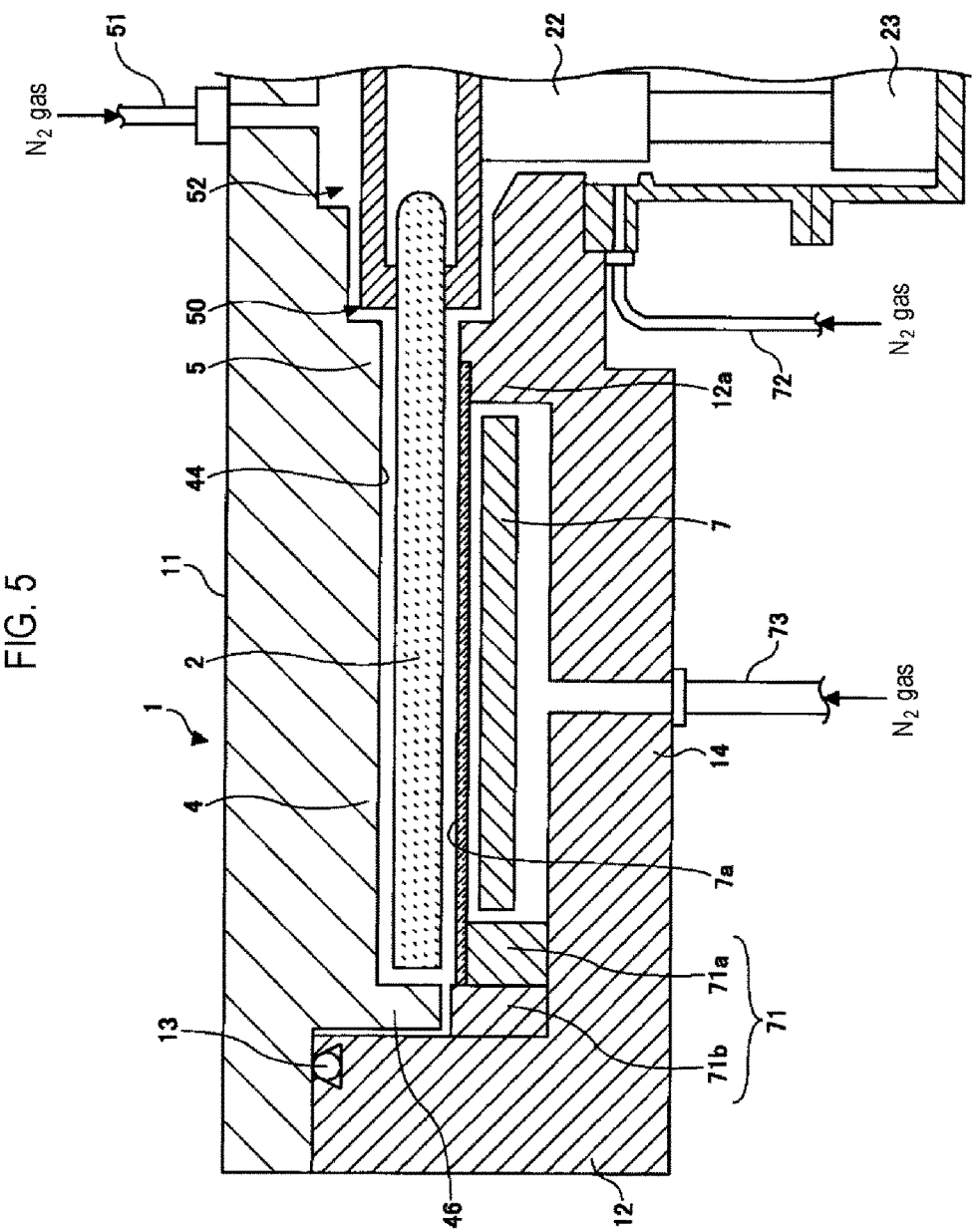
FIG. 5 is another schematic sectional view of the film forming apparatus shown in FIG. 1.

FIG. 1 referred to above is a sectional view taken along line I-I' in FIG. 3 and shows a region where the ceiling surface 45 is provided. On the other hand, FIG. 5 is a sectional view showing a region where the ceiling surface 44 is provided. As shown in FIG. 5, in the peripheral edge portion (the portion on the outer edge side of the vacuum container 1) of the fan-shaped convex portion 4, there is formed a bent portion 46 that bends in an L shape so as to face the outer end surface of the rotary table 2. Similar to the convex portion 4, the bent portion 46 suppresses the entry of the reaction gases from both sides of the separation region D and suppresses the mixing of both reaction gases. Since the fan-shaped convex portion 4 is provided on the top plate 11 and the top plate 11 can be removed from the container body 12, a slight gap exists between the outer peripheral surface of the bent portion 46 and the container body 12. The gap between the inner peripheral surface of the bent portion 46 and the outer end surface of the rotary table 2 and the gap between the outer peripheral surface of the bent portion 46 and the container body 12 are set to be the same as the height of the ceiling surface 44 with respect to the upper surface of the rotary table 2.

In the separation region D, the inner peripheral wall of the container body 12 is formed as a vertical surface close to the outer peripheral surface of the bent portion 46 as shown in FIG. 4. On the other hand, in the portion other than the separation region D, as shown in FIG. 1, the inner peripheral wall of the container body 12 is recessed outward, for example, from the portion facing the outer end surface of the rotary table 2 throughout the bottom portion 14. Hereinafter, for the convenience of description, the recessed portion having a substantially rectangular cross-sectional shape will be referred to as an exhaust region. More specifically, the exhaust region communicating with the first processing region P1 will be referred to as a first exhaust region E1, and the region communicating with the second processing region P2 will be referred to as a second exhaust region E2. As shown in FIGS. 1 to 3, a first exhaust port 61 and a second exhaust port 62 are formed in the bottom portions of the first exhaust region E1 and the second exhaust region E2, respectively. As shown in FIG. 1, each of the first exhaust port 61 and the second exhaust port 62 is connected to a vacuum exhaust means, for example, a vacuum pump 64 through an exhaust pipe 63. A pressure controller 65 is provided between the vacuum pump 64 and the exhaust pipe 63.

As shown in FIGS. 1 and 5, a heater unit 7 serving as a heating means is provided in the space between the rotary table 2 and the bottom portion 14 of the vacuum container 1. The wafer W on the rotary table 2 is heated to a temperature determined by a process recipe. On the lower side in the vicinity of the peripheral edge of the rotary table 2, a ring-shaped cover member 71 is provided (FIG. 5) in order to partition the atmosphere in a region extending from the upper space of the rotary table 2 to the first exhaust region E1 and the second exhaust region E2 and the atmosphere where the heater unit 7 is placed and to prevent a gas from entering the lower region of the rotary table 2. The cover member 71 includes an inner member 71a provided so that the inner member 71a faces the outer edge portion of the rotary table 2 and the outer peripheral side of the outer edge portion of the rotary table 2 from below, and an outer member 71b provided between the inner member 71a and the inner wall surface of the vacuum container 1. The outer member 71b is provided close to the bent portion 46 below the bent portion 46 formed in the outer edge portion of the convex portion 4 in the separation region D. The inner member 71a surrounds the entire circumference of the heater unit 7 below the outer edge portion of the rotary table 2 (and below the portion slightly outside the outer edge portion).

The bottom portion 14 closer to the rotation center than the space where the heater unit 7 is disposed protrudes upward so as to approach the core portion 21 in the vicinity of the center portion of the lower surface of the rotary table 2, thereby forming a projection portion 12a. A narrow space is formed between the projection portion 12a and the core portion 21. Furthermore, a narrow gap is formed between the inner circumferential surface of the through hole of the rotating shaft 22 passing through the bottom portion 14 and the rotating shaft 22. These spaces communicate with the case body 20. A purge gas supply pipe 72 for supplying an $N_2$ gas, which is a purge gas, into the narrow spaces and purging the narrow spaces is provided in the case body 20. A plurality of purge gas supply pipes 73 for purging the arrangement space of the heater unit 7 is provided in the bottom portion 14 of the vacuum container 1 at predetermined angular intervals in the circumferential direction under the heater unit 7 (one purge gas supply pipe 73 is shown in FIG. 5). In order to suppress the entry of a gas into the region where the heater unit 7 is provided, a lid member 7a that covers a gap between the inner wall surface of the outer member 71b (the upper surface of the inner member 71a) and the upper end portion of the projection portion 12a in the circumferential direction is provided between the heater unit 7 and the rotary table 2. The lid member 7a may be made of quartz, for example.

In addition, a separation gas supply pipe 51 is connected to the central portion of the top plate 11 of the vacuum container 1 and is configured to supply an $N_2$ gas, which is a separation gas, to a space 52 between the top plate 11 and the core portion 21. The separation gas supplied to the space 52 is discharged toward the peripheral edge along the wafer mounting region side surface of the rotary table 2 via a narrow space 50 between the protrusion portion 5 and the rotary table 2. The space 50 may be maintained at a higher pressure than the space 48 and the space 49 by the separation gas. Therefore, the space 50 suppresses the silicon-containing gas supplied to the first processing region P1 and the nitrogen-containing gas supplied to the second processing region P2 from passing through the central region C and being mixed each other. In other words, the space 50 (or the central region C) may function just like the separation space H (or the separation region D).

As shown in FIGS. 2 and 3, on the side wall of the vacuum container 1, there is formed the transfer port 15 for delivering a wafer W, which is a substrate, between an external transfer arm 10 and the rotary table 2. The transfer port 15 is opened and closed by a gate valve (not shown). In the recess 24 which is the wafer mounting region of the rotary table 2, the wafer W is delivered to and from the transfer arm 10 at a position facing the transfer port 15. Therefore, in a region corresponding to the delivery position on the lower side of the rotary table 2, there are provided delivery-purpose lift pins (not shown) penetrating the recess 24 to lift the wafer W from the back surface thereof and a lift mechanism (not shown) for the lift pins.

As shown in FIG. 1, the film forming apparatus according to the present embodiment includes a control part 100 formed of a computer for controlling the overall operation of the apparatus. In the memory of the control part 100, there is stored a program for causing the film forming apparatus to execute the method of forming a silicon nitride film described below under the control of the control part 100. In the program, step groups are incorporated so as to execute the method of forming a silicon nitride film described later. The program is stored in a medium 102 such as a hard disk, a compact disk, a magneto-optical disk, a memory card, a flexible disk or the like. The program is read into a memory part 101 by a predetermined reading device and is installed in the control part 100.

(Method of Forming Silicon Nitride Film)

Next, a method of forming a silicon nitride film according to an embodiment of the present disclosure will be described. The method of forming a silicon nitride film according to the embodiment of the present disclosure is a method of forming a silicon nitride film on the surface of a wafer W by using an ALD (Atomic Layer Deposition) method in which an adsorption step and a nitriding step are repeated. The adsorption step is a step in which a silicon-containing gas represented by a general formula $XSiCl_3$ (wherein X is an element whose bonding energy with Si is smaller than that of a Si—Cl bond) is supplied into the vacuum container 1 accommodating the wafer W to cause the silicon-containing gas to be adsorbed to the surface of the wafer W. As the silicon-containing gas, any gas may be used as long as it is represented by the general formula $XSiCl_3$ (wherein X is an element whose bonding energy with Si is smaller than that of a Si—Cl bond). Examples of the silicon-containing gas include trichlorosilane ($HSiCl_3$), $BrSiCl_3$ and $ISiCl_3$. The nitriding step is a step in which a nitrogen-containing gas is supplied into the vacuum container 1 to deposit an atomic layer or a molecular layer of a reaction product of the silicon-containing gas and the nitrogen-containing gas.

Figure 6:
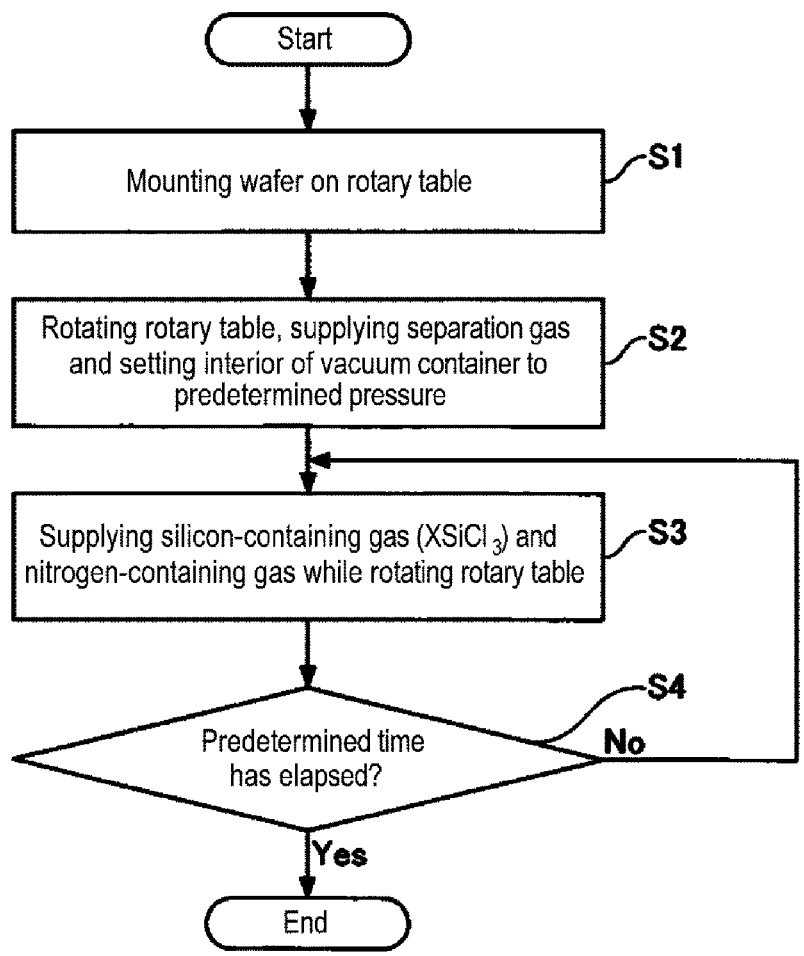
FIG. 6 is a flowchart showing a method of forming a silicon nitride film according to an embodiment of the present disclosure.

Hereinafter, a case where the above-described film forming apparatus is used will be described as an example with reference to FIG. 6. The method of forming a silicon nitride film according to the embodiment of the present disclosure may be carried out by using another film forming apparatus. FIG. 6 is a flowchart showing the method of forming a silicon nitride film according to the embodiment of the present disclosure.

First, in step S1, the wafer W is mounted on the rotary table 2. Specifically, a gate valve (not shown) is opened, and the wafer W is delivered from the outside to the recess 24 of the rotary table 2 via the transfer port 15 (FIGS. 2 and 3) by the transfer arm 10 (FIG. 3). The delivery of the wafer W is performed by raising and lowering the lift pins (not shown) from the bottom side of the vacuum container 1 via the through holes of the bottom surface of the recess 24 when the recess 24 is stopped at a position facing the transfer port 15. Such delivery of the wafer W is performed by intermittently rotating the rotary table 2 so that the wafer W is mounted in each of the five recesses 24 of the rotary table 2.

Subsequently, the gate valve is closed, and the interior of the vacuum container 1 is evacuated to a reachable degree of vacuum by the vacuum pump 64. Thereafter, in step S2, an $N_2$ gas is supplied from the separation gas nozzles 41 and 42 at a predetermined flow rate. An $N_2$ gas is also supplied from the separation gas supply pipe 51 and the purge gas supply pipes 72 and 73 at a predetermined flow rate. Along with this, the interior of the vacuum container 1 is controlled to be a preset processing pressure by the pressure controller 65 (FIG. 1). Next, the wafer W is heated to a predetermined temperature (for example, 400 degrees C. to 850 degrees C.) by the heater unit 7 while rotating the rotary table 2 clockwise, for example, at a rotation speed of 20 rpm.

Thereafter, in step S3, a silicon-containing gas represented by a general formula $XSiCl_3$ (wherein X is an element whose bonding energy with Si is smaller than that of a Si—Cl bond) is supplied from the reaction gas nozzle 31 (FIGS. 2 and 3), and a nitrogen-containing gas (for example, ammonia ($NH_3$)) is supplied from the reaction gas nozzle 32. By the rotation of the rotary table 2, the wafer W passes through the first processing region P1, the separation region D (separation space H), the second processing region P2, and the separation region D (separation space H) in the named order (FIG. 3). First, in the first processing region P1, the silicon-containing gas from the reaction gas nozzle 31 is adsorbed to the wafer W (adsorption step). Next, when the wafer W reaches the second processing region $P_2$ through the separation space H (separation region D) kept in an $N_2$ gas atmosphere, the silicon-containing gas adsorbed to the wafer W reacts with the nitrogen-containing gas supplied from the reaction gas nozzle 32, whereby a silicon nitride film is formed on the wafer W (nitriding step). Then, the wafer W reaches the separation region D (the separation space H kept in the $N_2$ gas atmosphere). The rotary table 2 is rotated a predetermined number of times, and the cycle is repeated a plurality of times. In this way, in step S3, the silicon-containing gas and the nitrogen-containing gas are alternately supplied to the surface of the wafer W.

In the meantime, it is determined whether or not the silicon-containing gas from the reaction gas nozzle 31 and the nitrogen-containing gas from the reaction gas nozzle 32 have been supplied for a predetermined time (step S4). The predetermined time is set depending on the target film thickness of the silicon nitride film to be formed on the surface of the wafer W. If the target film thickness is determined, the time of the step of forming the silicon nitride film may be appropriately determined in consideration of the conditions such as the rotation speed of the rotary table 2, the flow rates of the silicon-containing gas and the nitrogen-containing gas, the wafer temperature and the like.

If it is determined in step S4 that the predetermined time has not elapsed, the process returns to step S3 to continue the silicon nitride film forming process (the adsorption step and nitriding step). On the other hand, if the predetermined time has elapsed, the supply of the silicon-containing gas and the nitrogen-containing gas is stopped to terminate the film formation.

As described above, in the method of forming a silicon nitride film according to the embodiment of the present disclosure, in the adsorption step, the silicon-containing gas represented by the general formula $XSiCl_3$ (wherein X is an element whose bonding energy with Si is smaller than that of a Si—Cl bond) is supplied to cause the silicon-containing gas to be adsorbed to the surface of the wafer W. Accordingly, when the Si-containing gas is adsorbed to the surface of the wafer W, a Si—X bond is broken because the Si—X bond in $XSiCl_3$ is weaker than a Si—Cl bond. That is to say, three functional groups become chloro groups (Cl—). Therefore, the surface to which the silicon-containing gas is adsorbed has a structure in which the electron density on a silicon atom (Si) decreases and the silicon atom (Si) is likely to make a bond with a nitrogen atom (N) in an electrophilic manner. Thus, the surface is easily nitrided by the nitrogen-containing gas such as $NH_3$ or the like. As a result, in the nitriding step performed after the adsorption step, the reaction rate of the silicon-containing gas and the nitrogen-containing gas is improved and the productivity is enhanced. In addition, the three-dimensional structure of SiN is easily formed. Therefore, the film quality is improved.

In addition, the unreacted bonding sites on the surface of the wafer W are reduced by increasing the adsorption rate and the nitriding rate. Therefore, the variation in deposition rate is reduced in the plane of the wafer W, whereby the in-plane uniformity is improved.

Furthermore, since the three-dimensional structure of SiN is easily formed, since the film grows like a tree. As a result, the reaction surface on which the adsorption of the silicon-containing gas and the nitriding of the silicon-containing gas are performed is enlarged. Thus, the time (incubation time) until the film begins to grow on the surface of the wafer W is shortened.

EXAMPLE

Next, an Example and a Comparative Example conducted to confirm the effect of the silicon nitride film will be described. In the Example and the Comparative Example, silicon nitride films were formed under the following process conditions. In addition, the characteristics of the silicon nitride films formed in the Example and the Comparative Example were evaluated.

Example

Figure 7:
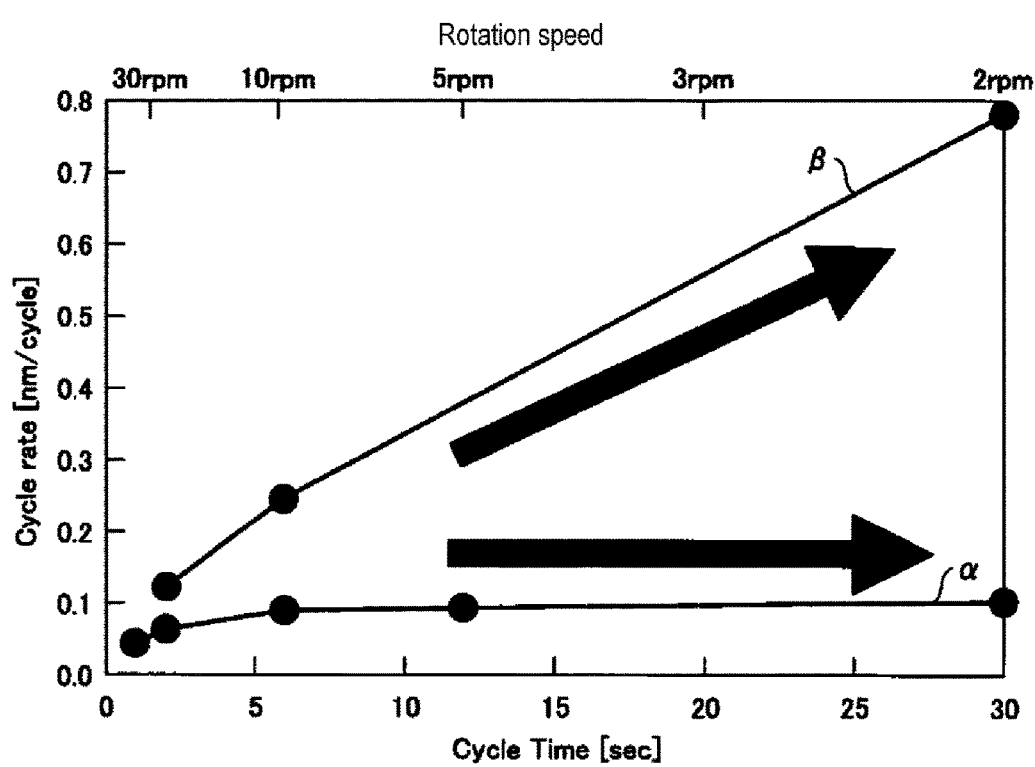
FIG. 7 is a diagram showing the cycle time dependency of a deposition rate of a silicon nitride film.

Silicon-containing gas: trichlorosilane ($HSiCl_3$) (hereinafter also referred to as "TrCS")
Nitrogen-containing gas: ammonia ($NH_3$)
Pressure: 4.0 Torr (533 Pa)
Wafer temperature: 760 degrees C.
Rotation speed of rotary table: 2 rpm, 5 rpm, 10 rpm, 30 rpm, and 60 rpm Comparative Example Silicon-containing gas: dichlorosilane ($H_2SiCl_2$) (hereinafter also referred to as "DCS")
Nitrogen-containing gas: ammonia ($NH_3$)
Pressure: 4.0 Torr (533 Pa)
Wafer temperature: 760 degrees C.
Rotation speed of rotary table 2: 2 rpm, 10 rpm, and 30 rpm FIG. 7 is a diagram showing the cycle time dependency of the deposition rate of the silicon nitride film. In FIG. 7, the horizontal axis represents the cycle time [sec] and the rotation speed [rpm], and the vertical axis represents the cycle rate [nm/cycle]. The cycle time refers to the time during which the rotary table 2 makes one revolution. The rotation speed refers to the rotation speed of the rotary table 2. The cycle rate refers to the thickness of a film formed while the rotary table 2 makes one revolution. In FIG. 7, the cycle rate of the silicon nitride film (Example) in the case of using TrCS as the silicon-containing gas is indicated by a characteristic line α, and the cycle rate of the silicon nitride film (Comparative Example) in the case of using DCS as the silicon-containing gas is indicated by a characteristic line β.

As shown in FIG. 7, when TrCS indicated by the characteristic line α is used, the cycle rate is hardly changed even if the cycle time is increased. From this result, it is considered that the silicon nitride film is formed by the deposition of each atomic layer attributable to an ALD reaction without thermal decomposition of TrCS.

On the other hand, in the case of using DCS indicated by the characteristic line β, if the cycle time is lengthened, the cycle rate increases as the cycle time increases. From this result, it is considered that thermal decomposition of DCS occurs and the silicon nitride film is formed by a CVD reaction.

Figure 8:
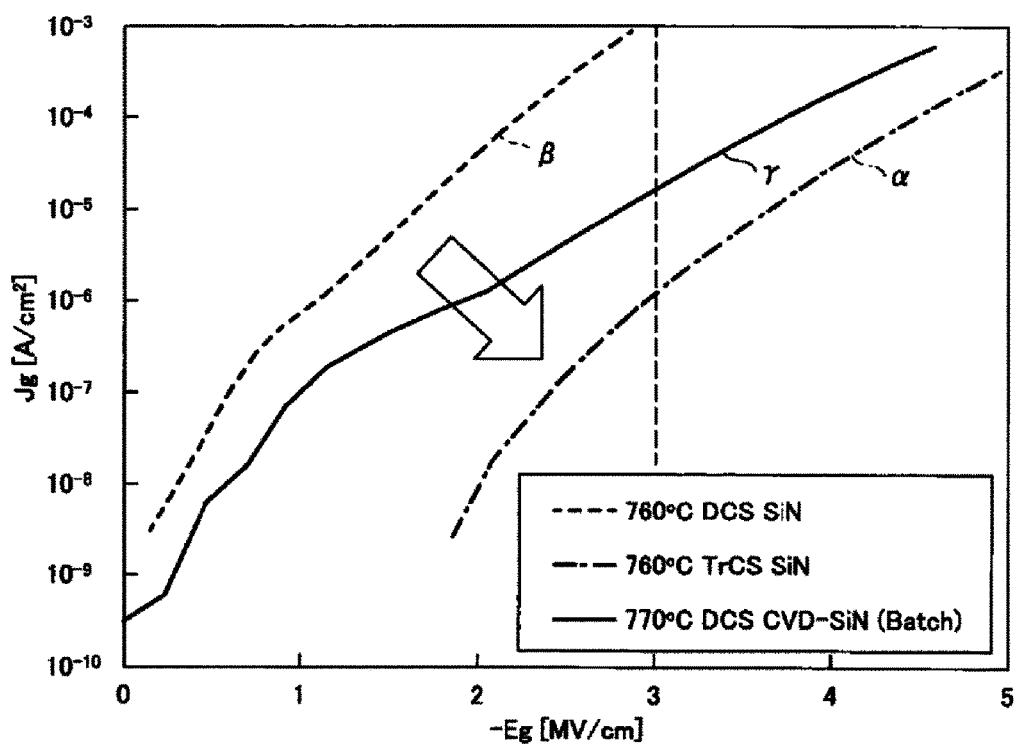
FIG. 8 is a diagram showing the leakage current characteristics of a silicon nitride film.

FIG. 8 is a diagram showing the leakage current characteristics of the silicon nitride film, and shows the electric field strength dependency of the current density when an electric field is applied to the silicon nitride film. In FIG. 8, the horizontal axis represents the electric field intensity $E_g$ [MV/cm] and the vertical axis represents the current density $J_g$ [A/cm$^2$]. The electric field intensity refers to the intensity of an electric field applied in the film thickness direction of the silicon nitride film. The current density refers to a current per 1 cm$^2$ flowing when an electric field is applied in the film thickness direction of the silicon nitride film. In FIG. 8, the Jg-Eg characteristics of the silicon nitride film (Example) in the case of using TrCS as the silicon-containing gas are indicated by a characteristic line α, and the Jg-Eg characteristics of the silicon nitride film (Comparative Example) in the case of using DCS as the silicon-containing gas are indicated by a characteristic line β. In addition, the Jg-Eg characteristics of the silicon nitride film formed by the CVD method (wafer temperature: 770 degrees C.) using a batch type heat treatment apparatus are indicated by a characteristic line γ.

As shown in FIG. 8, when TrCS indicated by the characteristic line α is used, the current density Jg is reduced as compared with the case where DCS indicated by the characteristic line β is used. Specifically, the current density Jg when an electric field of 3 [MV/cm] is applied to the silicon nitride film formed using TrCS indicated by the characteristic line α is $1.7 \times 10^{-6}$ [A/cm$^2$]. In contrast, the current density Jg when an electric field of 3 [MV/cm] is applied to the silicon nitride film formed using DCS indicated by the characteristic line β is $1.0 \times 10^{-3}$ [A/cm$^2$]. In other words, the silicon nitride film formed using TrCS is smaller in leakage current and more excellent in insulation property than the silicon nitride film formed using DCS. In addition, the current density is lower than the current density Jg available when an electric field of 3 [MV/cm] is applied to the silicon nitride film formed by a CVD method using a batch type heat treatment apparatus.

Figure 9:
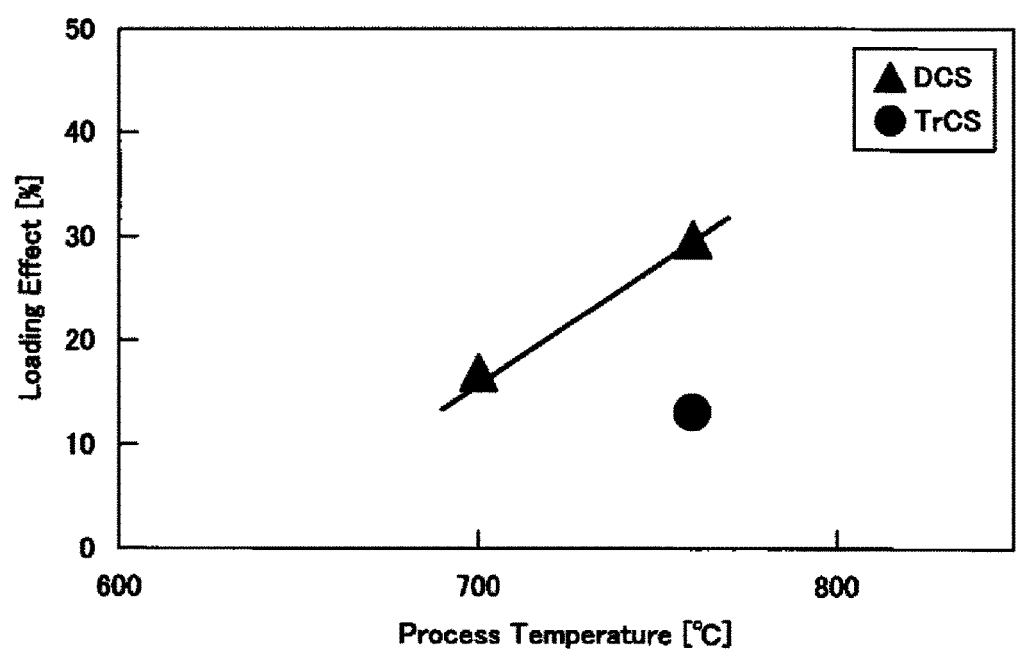
FIG. 9 is a diagram showing the relationship between the temperature of a wafer and the loading effect.

FIG. 9 is a diagram showing the relationship between the temperature of the wafer and the loading effect. In FIG. 9, the horizontal axis represents the wafer temperature [degrees C.] and the vertical axis represents the loading effect [%]. The loading effect in FIG. 9 refers to the ratio of the film thickness of the silicon nitride film formed on the surface of a wafer (patterned wafer) having an uneven pattern on the surface thereof to the film thickness of the silicon nitride film formed on the surface of a bare (mirror surface) wafer. In FIG. 9, the result obtained in the case of using TrCS as the silicon-containing gas is indicated by circular marks, and the result obtained in the case of using DCS is indicated by triangular marks.

As shown in FIG. 9, the loading effect when the wafer temperature is 760 degrees C. and the silicon-containing gas is TrCS is about 10%, whereas the loading effect when the wafer temperature is 760 degrees C. and the silicon-containing gas is DCS is about 30%. That is to say, by using TrCS as the silicon-containing gas, it is possible to suppress the loading effect at a high temperature (for example, 760 degrees C.).

In the above-described embodiment, the vacuum container 1 is an example of a processing chamber. In addition, the reaction gas nozzle 31 is an example of a first processing gas supply part, and the reaction gas nozzle 32 is an example of a second processing gas supply part. Furthermore, the separation region D is an example of an inert gas supply region, and the nitriding step is an example of a reaction step.

[Second Embodiment]

In the second embodiment, as another example of the method of forming a silicon nitride film of the present disclosure, a case where a silicon nitride film is formed by using a batch type film forming apparatus that performs a film forming process in units of one batch constituted by a large number of wafers mounted on a wafer boat will be described as an example.

(Film Forming Apparatus)

Figure 10:
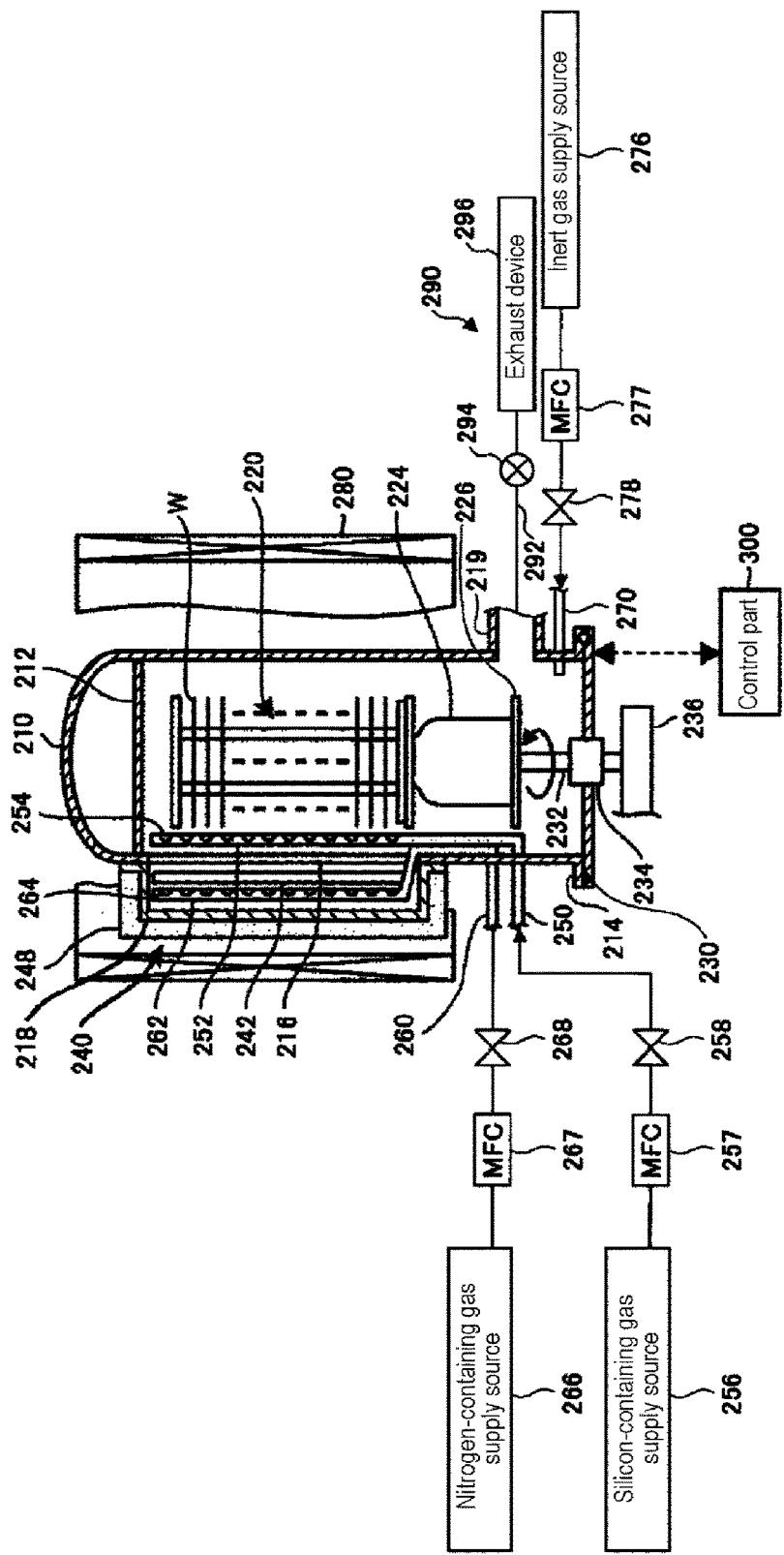
FIG. 10 is a schematic view of another example of a film forming apparatus suitable for carrying out a method of forming a silicon nitride film according to an embodiment of the present disclosure.
Figure 11:
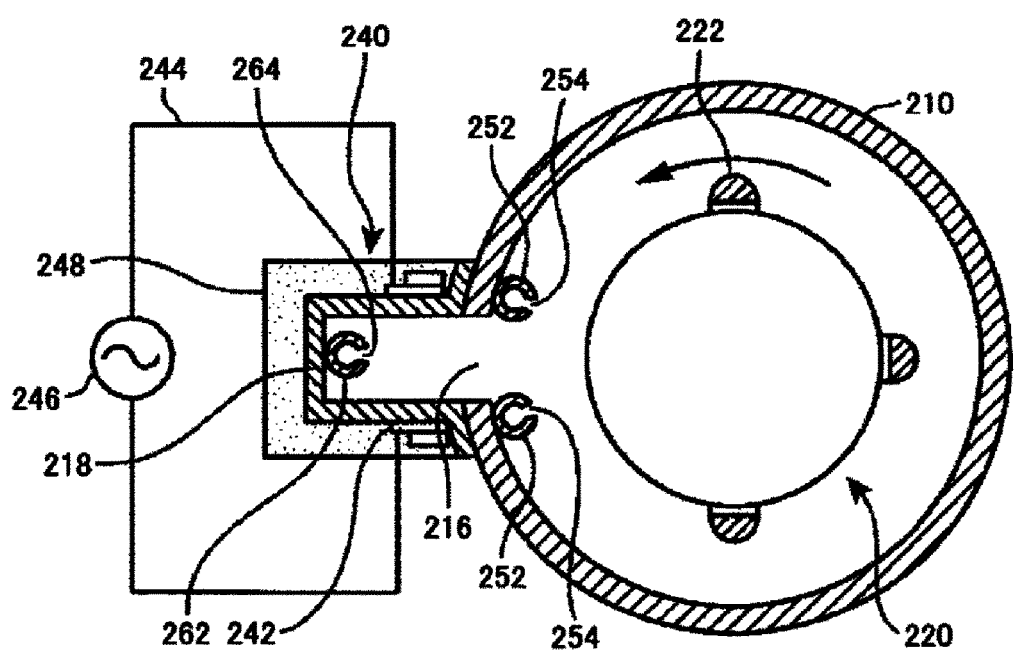
FIG. 11 is a schematic view of another example of a film forming apparatus suitable for carrying out a method of forming a silicon nitride film according to an embodiment of the present disclosure.

First, a film forming apparatus suitable for carrying out the method of forming a silicon nitride film according to the embodiment of the present disclosure will be described. FIGS. 10 and 11 are schematic views of another example of the film forming apparatus suitable for carrying out the method of forming a silicon nitride film according to the embodiment of the present disclosure. FIG. 10 shows a vertical cross section of the film forming apparatus, and FIG. 11 shows a horizontal cross section of the film forming apparatus.

As shown in FIG. 10, the film forming apparatus of the second embodiment includes a cylindrical processing container 210 having a ceiling and an open lower end. The processing container 210 is an example of a processing chamber. The processing container 210 is made of quartz, for example. The ceiling side of the processing container 210 is sealed by a quartz-made top plate 212. A flange portion 214 is provided in the opening at the lower end of the processing container 210. A stainless steel manifold may be provided at the lower end of the processing container 210.

In the opening at the lower end of the processing container 210, a wafer boat 220, which is a substrate holder for substantially horizontally holding a plurality of wafers W at predetermined intervals in the vertical direction, is loaded and unloaded.

As shown in FIG. 11, the wafer boat 220 includes, for example, three support columns 222. The wafer boat 220 substantially horizontally holds a plurality of (for example, 125) wafers W at predetermined intervals while supporting the outer edge portions of the wafers W. The wafer boat 220 is placed on a table 226 via a quartz-made heat insulating cylinder 224. The table 226 is supported by a rotating shaft 232 that penetrates a lid 230 made of stainless steel. When the wafer boat 220 is loaded into the processing container 210 through the opening of the processing container 210 and raised to a predetermined height position, the opening is airtightly closed by the lid 230.

At a position where the rotating shaft 232 penetrates the lid 230, there is provided a bearing portion 234 provided with, for example, a magnetic fluid seal and configured to rotatably hold the rotating shaft 232 while maintaining airtightness of the interior of the processing container 210. For example, an 0 ring is interposed between the peripheral portion of the lid 230 and the flange portion 214 of the processing container 210 to keep airtightness of the interior of the processing container 210.

The rotating shaft 232 is attached to the tip of an arm 236 supported by an elevating mechanism (not shown) such as, for example, a boat elevator. The elevating mechanism can raise and lower the wafer boat 220, the lid 230 and the like as a unit and can load and unload them into and from the processing container 210.

A plasma generating mechanism 240 is provided on a part of the side wall of the processing container 210. The plasma generating mechanism 240 is formed by airtightly joining, for example, a quartz-made partition wall 218 having a recessed cross-sectional shape, to the outer wall of the processing container 210 so as to cover a vertically elongated opening 216 formed in the side wall of the processing container 210. The opening 216 is formed to be elongated in the vertical direction so as to cover all the wafers W supported by the wafer boat 220.

A pair of plasma electrodes 242 facing each other is provided on the outer side surfaces of both side walls of the partition wall 218 along the length direction thereof (the vertical direction). A high-frequency power source 246 for plasma generation is connected to the plasma electrodes 242 via a power supply line 244. By applying a high-frequency voltage of, for example, 13.56 MHz to the plasma electrodes 242, plasma can be generated. Furthermore, for example, an insulating protective cover 248 made of quartz is attached to the outside of the partition wall 218 so as to cover the partition wall 218.

A gas supply pipe 250 for supplying a silicon-containing gas is inserted into the lower part of the processing container 210. For example, two gas nozzles 252 are provided at the tip portion of the gas supply pipe 250 so as to extend upward in the processing container 210. The gas nozzles 252 are made of a quartz tube and are disposed on both sides of the opening 216 of the plasma generating mechanism 240 so as to sandwich the opening 216 as shown in FIG. 11. In the gas nozzles 252, a plurality of gas discharge holes 254 is formed at predetermined intervals along the length direction thereof. The base end side of the gas supply pipe 250 is connected to a silicon-containing gas supply source 256. A mass flow controller 257, a valve 258 and the like are installed in the gas supply pipe 250.

In addition, a gas supply pipe 260 for supplying a nitrogen-containing gas is inserted into the lower part of the processing container 210. At the tip of the gas supply pipe 260, a gas nozzle 262 made of a quartz tube is provided. As shown in FIGS. 10 and 11, the gas nozzle 262 extends upward within the processing container 210. The gas nozzle 262 is bent in the middle thereof and is disposed in the plasma generating mechanism 240. In addition, a plurality of gas discharge holes 264 is formed in the gas nozzle 262 at predetermined intervals along the length direction thereof. The base end side of the gas supply pipe 260 is connected to a nitrogen-containing gas supply source 266. A mass flow controller 267, a valve 268 and the like are installed in the gas supply pipe 260.

A straight tubular quartz-made gas supply pipe 270 for supplying an inert gas is inserted into the lower part of the processing container 210. The base end portion of the gas supply pipe 270 is connected to an inert gas supply source 276. A mass flow controller 277, a valve 278 and the like are installed in the gas supply pipe 270.

In FIG. 10, for the convenience of illustration, the gas nozzles 252, the gas nozzle 262 and the gas supply pipe 270 are shown to be inserted into the processing container 210 through the side wall on the lower side of the processing container 210. However, in reality, they are inserted through the flange portion 214.

Around the processing container 210, a cylindrical heater 280 is provided so as to surround the side circumferential surface of the processing container 210 from the outside. The heater 280 is configured to heat the wafers W in the processing container 210 to a predetermined temperature (for example, 400 degrees C. to 850 degrees C.).

An exhaust port 219 is formed on the side wall surface on the lower side of the processing container 210. An exhaust part 290 is provided in the exhaust port 219. The exhaust part 290 includes an exhaust passage 292 connected to the exhaust port 219. A pressure regulation valve 294 and an exhaust device 296 such as a vacuum pump or the like are sequentially installed in the exhaust passage 292 to evacuate the inside of the processing container 210 to vacuum.

As shown in FIG. 10, the film forming apparatus includes a control part 300. The control part 300 is composed of a computer having a CPU (not shown) and a memory part (not shown). A program incorporating a group of steps relating to the operation of the method of forming a silicon nitride film to be described later is recorded in the memory part. The program is stored in a storage medium and installed in the computer from the storage medium.

(Method of Forming Silicon Nitride Film)

Next, a method of forming a silicon nitride film according to a second embodiment will be described. As in the first embodiment, the method of forming a silicon nitride film according to the second embodiment is a method of forming a silicon nitride film on the surface of the wafer W by using an ALD (Atomic Layer Deposition) method in which an adsorption step and a nitriding step are repeated. The adsorption step is a step in which a silicon-containing gas (raw material gas) represented by a general formula $XSiCl_3$ (wherein X is an element whose bonding energy with Si is smaller than that of a Si—Cl bond) is supplied into a vacuum container accommodating the wafer W to cause the silicon-containing gas to be adsorbed to the surface of the wafer W. As the silicon-containing gas, any gas may be used as long as it is represented by the general formula $XSiCl_3$ (wherein X is an element whose bonding energy with Si is smaller than that of a Si—Cl bond). Examples of the silicon-containing gas include trichlorosilane ($HSiCl_3$), $BrSiCl_3$ and $ISiCl_3$. The nitriding step is a step in which a nitrogen-containing gas (reaction gas) is supplied into the vacuum container to deposit an atomic layer or a molecular layer of a reaction product of the silicon-containing gas and the nitrogen-containing gas.

Figure 12:
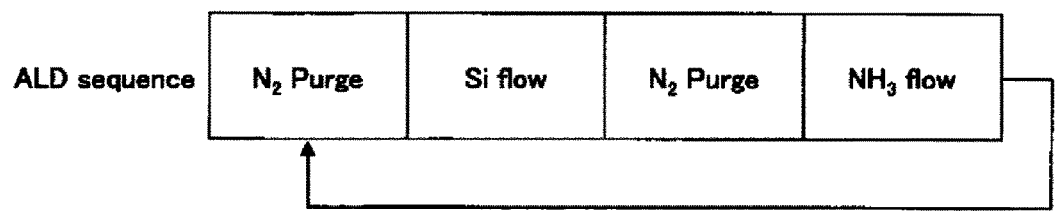
FIG. 12 is a diagram for explaining a method of forming a silicon nitride film according to a second embodiment.

Hereinafter, a case of using the above-described film forming apparatus will be described as an example with reference to FIG. 12. The method of forming a silicon nitride film according to the second embodiment may be carried out using another film forming apparatus. FIG. 12 is a diagram for explaining the method of forming a silicon nitride film according to the second embodiment.

As shown in FIG. 12, in the method of forming a silicon nitride film, a silicon nitride film having a desired thickness is formed by repeating, plural times, a cycle composed of a purging step, an adsorption step, a purging step and a nitriding step. In the adsorption step, a silicon-containing gas represented by a general formula $XSiCl_3$ (wherein X is an element whose bonding energy with Si is smaller than that of a Si—Cl bond) is supplied from the gas nozzle 252 (FIG. 10). In the nitriding step, a nitrogen-containing gas (for example, $NH_3$) is supplied from the gas nozzle 262 (FIG. 10). In the purging step, an inert gas (for example, $N_2$) is supplied from the gas supply pipe 270 (FIG. 10).

As described above, in the method of forming a silicon nitride film according to the second embodiment, in the adsorption step, the silicon-containing gas represented by the general formula $XSiCl_3$ (wherein X is an element whose bonding energy with Si is smaller than that of a Si—Cl bond) is supplied to cause the silicon-containing gas to be adsorbed to the surface of the wafer W. Accordingly, when the Si-containing gas is adsorbed to the surface of the wafer W, a Si—X bond is broken because the Si—X bond in $XSiCl_3$ is weaker than a Si—Cl bond. That is to say, three functional groups become chloro groups (Cl—). Therefore, the surface to which the silicon-containing gas is adsorbed has a structure in which the electron density on a silicon atom (Si) decreases and the silicon atom (Si) is likely to make a bond with a nitrogen atom (N) in an electrophilic manner. Thus, the surface is easily nitrided by the nitrogen-containing gas such as $NH_3$ or the like. As a result, in the nitriding step performed after the adsorption step, the reaction rate of the silicon-containing gas and the nitrogen-containing gas is improved and the productivity is enhanced. In addition, the three-dimensional structure of SiN is easily formed. Therefore, the film quality is improved.

In addition, the unreacted bonding sites on the surface of the wafer W are reduced by increasing the adsorption rate and the nitriding rate. Therefore, the variation in deposition rate is reduced in the plane of the wafer W, whereby the in-plane uniformity is improved.

Furthermore, since the three-dimensional structure of SiN is easily formed, the film grows like a tree. As a result, the reaction surface on which the adsorption of the silicon-containing gas and the nitriding of the silicon-containing gas are performed is enlarged. Thus, the time (incubation time) until the film begins to grow on the surface of the wafer W is shortened.

Next, an Example and a Comparative Example will be described. In the Example and the Comparative Example, silicon nitride films were formed under the following process conditions. In addition, the characteristics of the silicon nitride films formed in the Example and the Comparative Example were evaluated.

Example

Silicon-containing gas: TrCS
Nitrogen-containing gas: $NH_3$
Wafer temperature: 700 degrees C., 750 degrees C., and 800 degrees C.

Comparative Example

Silicon-containing gas: DCS
Nitrogen-containing gas: $NH_3$
Wafer temperature: 640 degrees C., 660 degrees C., and 700 degrees C.

Figure 13:
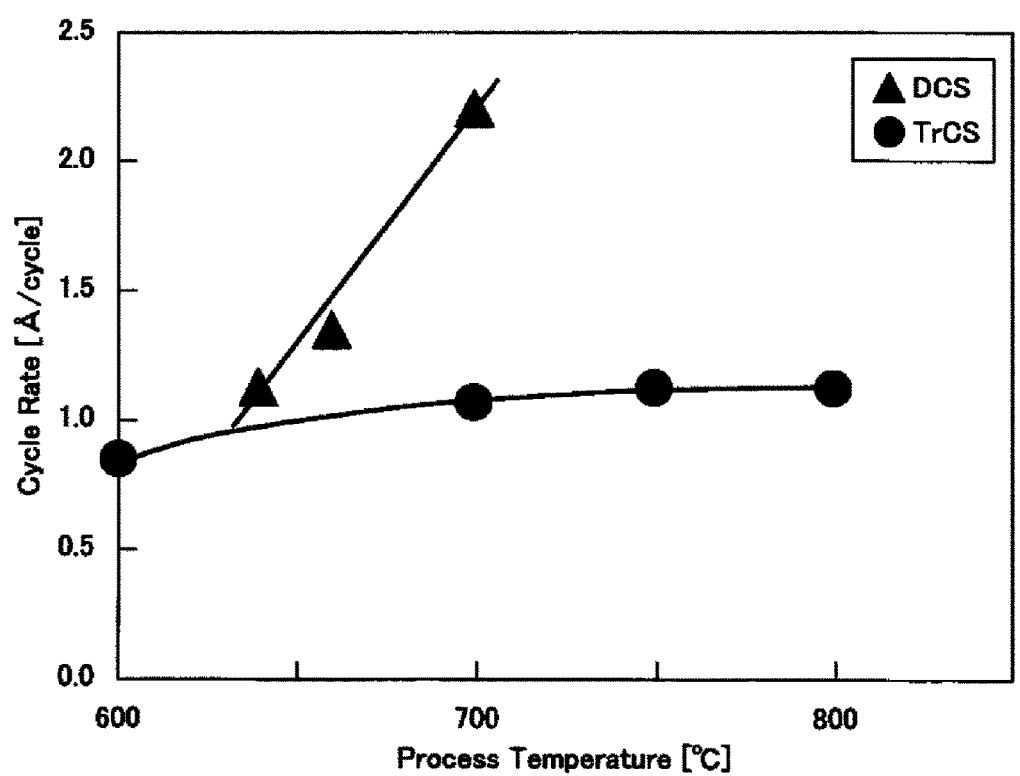
FIG. 13 is a diagram showing the relationship between the temperature of a wafer and the cycle rate of a silicon nitride film.

FIG. 13 is a diagram showing the relationship between the wafer temperature and the cycle rate of the silicon nitride film. In FIG. 13, the horizontal axis represents the wafer temperature [degrees C.] and the vertical axis represents the cycle rate [A/cycle]. Furthermore, in FIG. 13, the cycle rate of the silicon nitride film (Example) in the case of using TrCS as the silicon-containing gas is indicated by circular marks, and the cycle rate of the silicon nitride film (Comparative Example) in the case of using DCS as the silicon-containing gas is indicated by triangular marks.

As shown in FIG. 13, when TrCS is used, even if the wafer is heated to 800 degrees C., the cycle rate is hardly changed. From this result, it is considered that even if the wafer is heated to 800 degrees C., the TrCS is not thermally decomposed and the silicon nitride film is formed by the deposition of each atomic layer attributable to an ALD reaction. On the other hand, in the case of using DCS, when the wafer temperature is 640 degrees C., the same cycle rate as in the case of TrCS is obtained. However, as the wafer temperature increases, the cycle rate becomes high. From this result, it is considered that when the temperature of the wafer is higher than 640 degrees C., thermal decomposition of DCS occurs and a silicon nitride film is formed by a CVD reaction.

Figure 14:
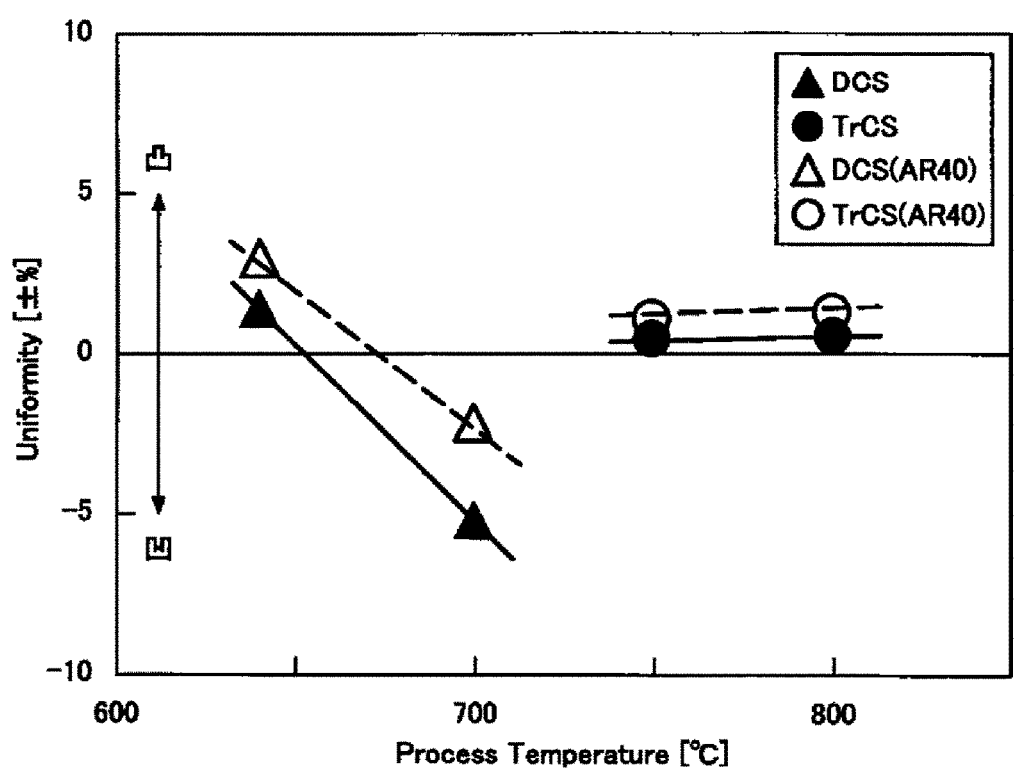
FIG. 14 is a diagram showing the relationship between the temperature of a wafer and the in-plane uniformity of a film thickness of a silicon nitride film.

FIG. 14 is a diagram showing the relationship between the wafer temperature and the in-plane uniformity of the film thickness of the silicon nitride film. In FIG. 14, the horizontal axis represents the wafer temperature [degrees C.] and the vertical axis represents the in-plane uniformity (±%) of the film thickness of the silicon nitride film. In FIG. 14, the in-plane distribution of a convex shape having a large film thickness at the central portion of the wafer and a small film thickness at the outer peripheral portion is shown as a positive value, and the in-plane distribution of a concave shape having a small film thickness at the central portion of the wafer and a large film thickness at the outer peripheral portion is shown as a negative value. In FIG. 14, the in-plane uniformity of the film thickness of the silicon nitride film (Example) in the case of using TrCS as the silicon-containing gas is indicated by circular marks, and the in-plane uniformity of the film thickness of the silicon nitride film (Comparative Example) in the case of using DCS as the silicon-containing gas is indicated by triangular marks. In addition, the black marks indicate the results obtained when the silicon nitride film was formed on the surface of a bare (mirror surface) wafer, and the white marks indicate the results obtained when the silicon nitride film was formed on the surface of the wafer on which a concavo-convex pattern having a surface area of forty times is formed.

As shown in FIG. 14, it was confirmed that in the case of using TrCS, regardless of whether the wafer temperature is 750 degrees C. or 800 degrees C., good in-plane uniformity of ±1% or less is obtained irrespective of the surface area of the wafer. On the other hand, it was confirmed that in the case of using DCS, regardless of whether the wafer temperature is 640 degrees C. or 700 degrees C., the deposition amount of the silicon nitride film in the wafer plane varies depending on the surface area of the wafer. From this result, it is considered that by using TrCS, as compared with the case of using DCS, it is possible to suppress the so-called loading effect in which the deposition amount in the wafer plane fluctuates depending on the surface area on the wafer.

Figure 15:
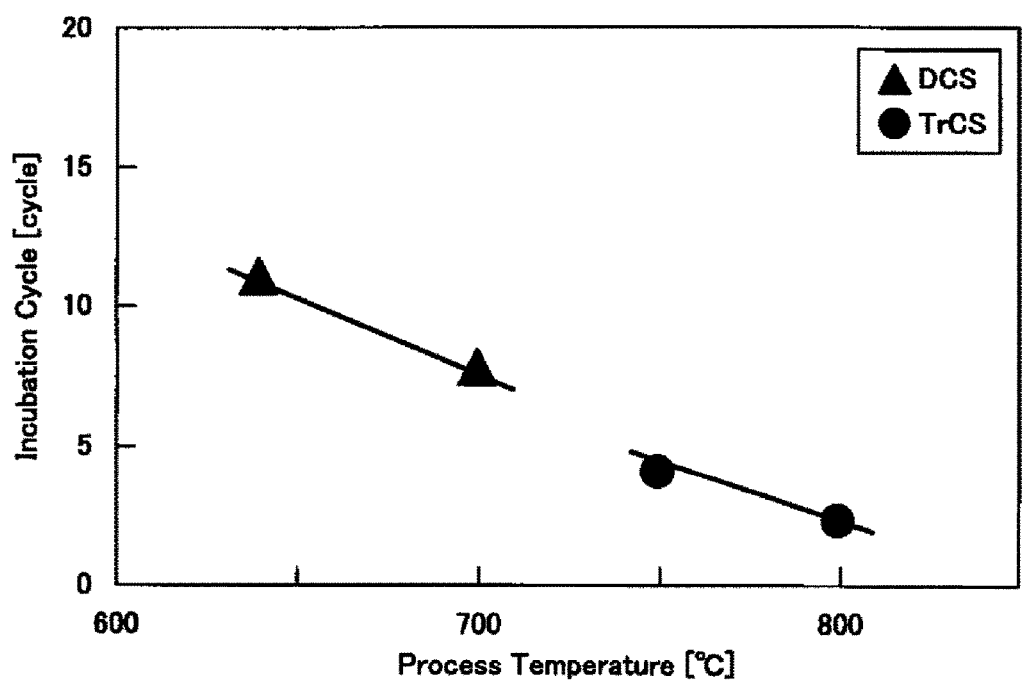
FIG. 15 is a diagram showing the relationship between the temperature of a wafer and the incubation cycle.

FIG. 15 is a diagram showing the relationship between the wafer temperature and the incubation cycle. In FIG. 15, the horizontal axis represents the wafer temperature [degrees C.] and the vertical axis represents the incubation cycle [cycle]. In FIG. 15, the incubation time in the case of using TrCS as the silicon-containing gas is indicated by circular marks, and the incubation time in the case of using DCS as the silicon-containing gas is indicated by triangular marks.

As shown in FIG. 15, it was confirmed that by using TrCS, compared with the case of using DCS, the incubation cycle (time) can be shortened to one half or less.

[Adsorption Mechanism]

Next, the mechanism of adsorbing the silicon-containing gas in the method of forming a silicon nitride film according to the embodiments of the present disclosure will be described by taking as an example the case of using $SiHCl_3$ as the silicon-containing gas.

Figure 16:
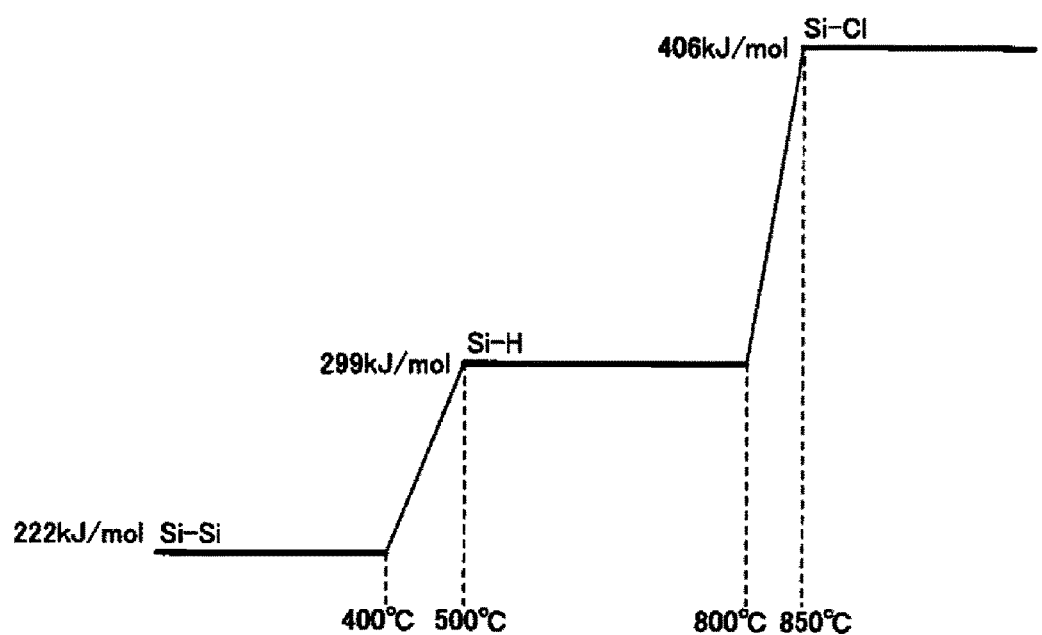
FIG. 16 is a diagram for explaining the bonding energy.

FIG. 16 is a diagram for explaining the bonding energy. As shown in FIG. 16, the bonding energies of a Si—Si bond, a Si—H bond, and a Si—Cl bond are 222 kJ/mol, 299 kJ/mol, and 406 kJ/mol, respectively. The Si—H bond is thermally decomposed in a temperature range of 400 degrees C. to 500 degrees C. or higher to release a hydrogen atom (H). In addition, the Si—Cl bond is thermally decomposed in a temperature range of 800 degrees C. to 850 degrees C. or higher to release a chlorine atom (Cl).

FIGS. 17A and 17B are diagrams for explaining the adsorption mechanism of the silicon-containing gas. FIG. 17A shows the adsorption mechanism when $SiH_2Cl_2$ (DCS) is used as the silicon-containing gas, and FIG. 17B shows the adsorption mechanism when $SiHCl_3$ (TrCS) is used as the silicon-containing gas.

As shown in FIG. 17A, in $SiH_2Cl_2$, when the wafer is heated to a temperature range (400 degrees C. to 500 degrees C. or higher) where a hydrogen atom (H) is released from a Si—H bond, two hydrogen atoms (H) are released and two dangling bonds are generated. At this time, one dangling bond is bonded and adsorbed to a nitrogen atom (N) on the surface of the wafer, and the other dangling bond is bonded to another $SiH_2Cl_2$ molecule. That is to say, excessive adsorption in which multiple layers of silicon are adsorbed during one cycle may occur.

On the other hand, as shown in FIG. 17B, in $SiHCl_3$, when the wafer is heated to a temperature range (for example, 400 degrees C. to 500 degrees C. or higher) in which a hydrogen atom (H) is released from a Si—H bond and to a temperature range (800 degrees C. to 850 degrees C. or lower) in which a chlorine atom (Cl) is not released from a Si—Cl bond, one hydrogen atom (H) is released and one dangling bond is generated. At this time, the dangling bond is bonded and adsorbed to a nitrogen atom (N) on the surface of the wafer. Since there is no other dangling bond, even if another SiHCl$_3$ reaches the surface to which SiHCl$_3$ is adsorbed, a new adsorption reaction does not proceed. That is to say, it is possible to prevent the occurrence of excessive adsorption in which multiple layers of silicon are adsorbed during one cycle. As a result, ideal ALD film formation can be realized, and a silicon nitride film with high quality and good in-plane uniformity can be formed. In view of the foregoing, in the adsorption step, the wafer is preferably heated to 400 degrees C. to 850 degrees C., more preferably 500 degrees C. to 800 degrees C.

[Application Example of Silicon Nitride Film]

An application example of the silicon nitride film according to the embodiments of the present disclosure will be described. The silicon nitride film according to the embodiments of the present disclosure may be suitably used as a charge storage layer (charge trap layer) for use in a three-dimensional NAND flash memory of a Si—SiO$_2$—SiN—SiO$_2$—Si structure (hereinafter referred to as "SONOS structure").

Figure 18:
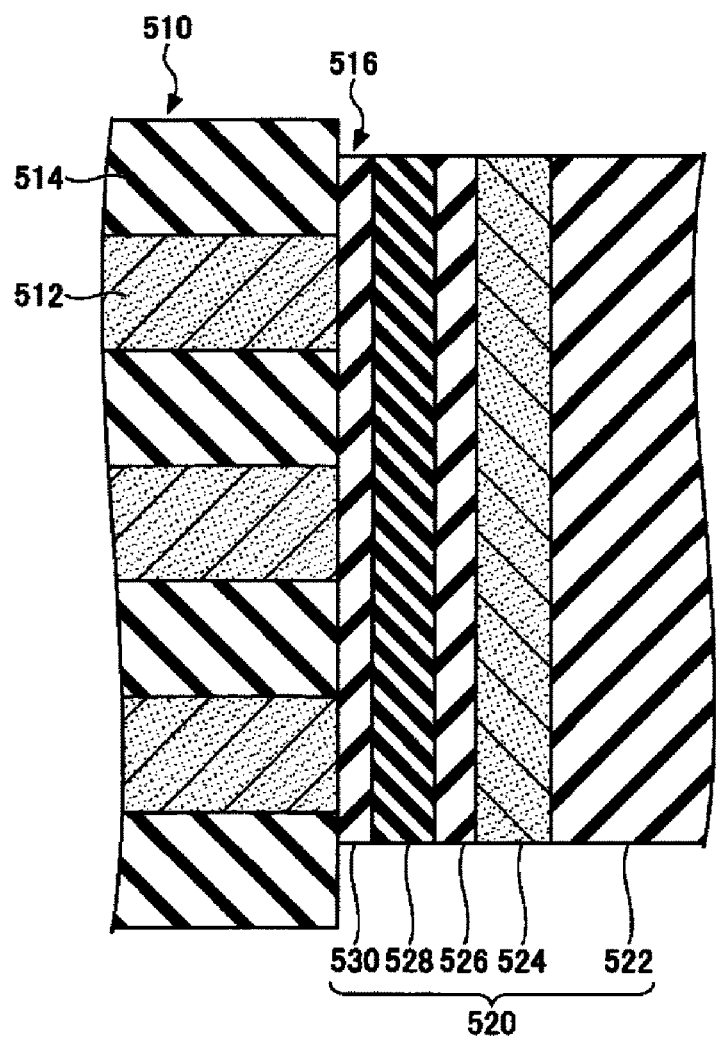
FIG. 18 is a view showing an example of a three-dimensional NAND flash memory with a SONOS structure.

FIG. 18 is a diagram showing an example of a three-dimensional NAND flash memory with a SONOS structure. As shown in FIG. 18, the three-dimensional NAND flash memory with a SONOS structure includes a stacked body 510 and a columnar body 520.

The stacked body 510 is formed by alternately stacking silicon layers 512 and silicon oxide films 514. A through-hole 516 penetrating in the stacking direction of the stacked body 510 is formed in the stacked body 510. The columnar body 520 is formed inside the through-hole 516. In FIG. 18, a part of the through-hole 516 is shown.

The columnar body 520 includes a columnar insulator 522, a channel layer 524, a tunnel insulating film 526, a charge storage layer 528, and a block insulating film 530.

The columnar insulator 522 is formed at the center of the columnar body 520. The columnar insulator 522 is formed of, for example, a silicon oxide film.

The channel layer 524 is formed between the outer surface of the columnar insulator 522 and the inner surface of the through-hole 516. The channel layer 524 is formed of a semiconductor such as, for example, silicon.

The tunnel insulating film 526 is formed between the inner surface of the through-hole 516 and the channel layer 524. The tunnel insulating film 526 is formed of, for example, a silicon oxide film.

The charge storage layer 528 is formed between the inner surface of the through-hole 516 and the tunnel insulating film 526. The charge storage layer 528 is formed of, for example, a silicon nitride film. If the charge storage layer 528 is formed of a silicon nitride film, it is preferable because the charge trapping sites in the film are increased. In addition, if the charge storage layer 528 is formed of a silicon nitride film, it is preferable because a high band barrier can be formed with respect to the silicon oxide film constituting the tunnel insulating film 526 and the block insulating film 530.

The block insulating film 530 is formed between the inner surface of the through-hole 516 and the charge storage layer 528. The block insulating film 530 is formed of, for example, a silicon oxide film.

Incidentally, a silicon nitride film with high quality and good in-plane uniformity is required for the charge storage layer 528 for use in a three-dimensional NAND flash memory with a SONOS structure. In addition, as the surface area increases due to pattern miniaturization, a silicon nitride film with a small loading effect is required.

As a method of forming a high-quality silicon nitride film, film formation by an ALD method at a high temperature (for example, 700 degrees C. or higher) is effective. However, silicon-containing gases such as Si$_2$HCl$_2$ (DCS) and Si$_2$H$_6$ (HCD) which have been conventionally used as raw material gases are autolyzed under a high temperature to cause excessive adsorption of Si. This makes it impossible to obtain good in-plane uniformity.

In contrast, in the method of forming a silicon nitride film according to the embodiments of the present disclosure, SiHCl$_3$ (TrCS) is used as a raw material gas. Thus, the dangling bond at the time of Si adsorption is limited to one. This makes it possible to prevent excessive adsorption and physical adsorption of Si. As a result, it is possible to realize ideal ALD film formation and to form a silicon nitride film with high quality and good in-plane uniformity.

While a mode for carrying out the present disclosure has been described above, the above descriptions do not limit the contents of the present disclosure. Various modifications and improvements may be made within the scope of the present disclosure.

In the above-described embodiments, a semiconductor wafer has been described as an example of a substrate. However, the present disclosure is not limited thereto. The present disclosure may also be applied to a glass substrate, an LCD substrate, a ceramic substrate, or the like.

In the above-described embodiments, the semi-batch type and batch type film forming apparatuses have been described as examples. However, the present disclosure is not limited thereto. It may be possible to use, for example, a single-wafer type film forming apparatus that performs a film forming process one by one.

In the above-described embodiments, a case where a silicon nitride film is formed as an example of a silicon-containing film has been described as an example. However, the present disclosure is not limited thereto. For example, the present disclosure may be applied to a case of forming a silicon oxide film or a silicon oxynitride film. In the case of forming a silicon oxide film, an oxygen-containing gas such as oxygen or ozone may be used as a reaction gas instead of the nitrogen-containing gas. In the case of forming a silicon oxynitride film, a nitrogen-containing gas and an oxygen-containing gas may be used as reaction gases.

According to the method of forming a silicon-containing film disclosed herein, it is possible to achieve both the enhancement in productivity and the improvement in film quality.

While certain embodiments have been described, these embodiments have been presented by way of example only, and are not intended to limit the scope of the disclosures. Indeed, the embodiments described herein may be embodied in a variety of other forms. Furthermore, various omissions, substitutions and changes in the form of the embodiments described herein may be made without departing from the spirit of the disclosures. The accompanying claims and their equivalents are intended to cover such forms or modifications as would fall within the scope and spirit of the disclosures.

What is claimed is:

1. A method of forming a silicon-containing film, comprising:
    an adsorption step of supplying a silicon-containing gas represented by a general formula XSiCl3 (wherein X is an element whose bonding energy with Si is smaller than bonding energy of a Si—Cl bond) into a processing chamber accommodating substrates to cause the silicon-containing gas to be adsorbed to a surface of each of the substrates; and a reaction step of supplying a reaction gas reacting with the silicon-containing gas into the processing chamber to cause the silicon-containing gas adsorbed to the surface of each of the substrates to react with the reaction gas, wherein by alternately repeating the adsorption step and the reaction step, a reaction product of the silicon-containing gas and the reaction gas is deposited on the surface of each of the substrates to form the silicon-containing film.

2. The method of claim 1, wherein in the adsorption step, the substrates are heated to a temperature of 400 degrees C. to 850 degrees C.

3. The method of claim 1, wherein the silicon-containing gas is one of HSiCl3, BrSiCL and ISiCl3.

4. The method of claim 1, wherein the silicon-containing gas is HSiCl3.

5. The method of claim 1, wherein the reaction gas is a nitrogen-containing gas.

6. The method of claim 5, wherein the nitrogen-containing gas is NH3.

7. The method of claim 1, further comprising: a purge step performed between the adsorption step and the reaction step to supply an inert gas to the substrates.

8. The method of claim 7, wherein the substrates are mounted on an upper surface of a rotatable rotary table along a circumferential direction of the rotary table, a first processing region in which the silicon-containing gas is supplied toward the upper surface of the rotary table and a second processing region in which the reaction gas is supplied toward the upper surface of the rotary table are provided along a rotation direction of the rotary table so as to be spaced apart from each other, and the adsorption step and the reaction step are executed by rotating the rotary table and causing the substrates to sequentially pass through the first processing region and the second processing region.

9. The method of claim 8, wherein an inert gas supply region in which the inert gas is supplied is provided between the first processing region and the second processing region, and the purge step is executed by causing the substrates to pass through the inert gas supply region.

10. The method of claim 7, wherein the substrates are held horizontally on a substrate holder at predetermined intervals in a vertical direction, and the adsorption step and the reaction step are executed by intermittently supplying the silicon-containing gas and the reaction gas into the processing chamber.

11. The method of claim 1, wherein a recess is formed on the surface of each of the substrates, and the silicon-containing film is formed in the recess.

* * * * *